United States Patent
Martin et al.

(10) Patent No.: US 10,935,543 B2
(45) Date of Patent: Mar. 2, 2021

(54) METHOD FOR DETERMINING FAT FREE BODY MASS

(71) Applicant: NESTEC S.A., Vevey (CH)

(72) Inventors: François-Pierre Martin, Vuisternens-devant-Romont (CH); Ornella Cominetti, Denges (CH); Jean-Philippe Godin, Ecublens (CH); Jessica Ezri, Lausanne (CH); Andreas Nydegger, Estavayer-le-Lac (CH)

(73) Assignee: Societe des Produits Nestle S.A., Vevey (CH)

( * ) Notice: Subject to any disclaimer, the term of this patent is extended or adjusted under 35 U.S.C. 154(b) by 248 days.

(21) Appl. No.: 15/778,738

(22) PCT Filed: Dec. 30, 2016

(86) PCT No.: PCT/EP2016/081841
§ 371 (c)(1),
(2) Date: May 24, 2018

(87) PCT Pub. No.: WO2017/114686
PCT Pub. Date: Jul. 6, 2017

(65) Prior Publication Data
US 2018/0356401 A1    Dec. 13, 2018

(30) Foreign Application Priority Data
Dec. 30, 2015 (EP) .................... 15203045

(51) Int. Cl.
*G01N 33/50* (2006.01)
*G01N 33/564* (2006.01)
G01N 24/08 (2006.01)
G01N 33/68 (2006.01)

(52) U.S. Cl.
CPC ......... *G01N 33/5091* (2013.01); *G01N 24/08* (2013.01); *G01N 33/564* (2013.01); *G01N 33/6893* (2013.01); *G01N 2800/02* (2013.01); *G01N 2800/044* (2013.01); *G01N 2800/065* (2013.01); *G01N 2800/52* (2013.01)

(58) Field of Classification Search
CPC ......... G01N 2800/044; G01N 2800/52; G01N 2800/02; G01N 2800/065; G01N 33/5091; G01N 33/564; G01N 33/6893
See application file for complete search history.

(56) References Cited

U.S. PATENT DOCUMENTS

2010/0286034 A1   11/2010   Broecke Van Den et al.
2012/0003158 A1*   1/2012   Alexander ........... G01N 33/564
                                                            424/9.2

FOREIGN PATENT DOCUMENTS

JP    H01143874 A    6/1989
JP    2011528117 A    11/2011
JP    2013504571 A    2/2013

OTHER PUBLICATIONS

"Tips to Decrease Body Fat and Increase Lean Muscle Mass." MIT website, archived by web.archive.org, <http://http://web.archive.org/web/20100107050205/https://web.mit.edu/21w785/F97/weights/menu/diet/DBF.html> archived 2010, obtained by the examiner May 11, 2020. (Year: 2010).*
Ezri et al; (2012) Impact of Disease and Treatments on Growth and Puberty of Pediatric Patients with Inflammatory Bowel Disease Digestion 85(4): 308-319.
Sauer CG and Kugathasan S, (2009) Pediatric inflammatory bowel disease: highlighting pediatric differences in IBD. Gastroenterol Clin North Am 38(4): 611-628.
Boot et al. Bone mineral density and nutritional status in children with chronic inflammatory bowel disease. Gut 25 42(2): 188-194; 1998.
Azcue et al. Energy expenditure and body composition in children with Crohn's disease: effect of enteral nutrition and treatment with prednisolone. Gut 41(2): 203-208; 1997.
Burnham et al. Body-composition alterations consistent with cachexia in children and young adults with Crohn disease. Am J Clin Nutr 82(2): 413-420; 2005.
Thayu et al. Gender differences in body composition deficits at diagnosis in children and adolescents with Crohn's disease. Inflamm Bowel Dis 13(9): 1121-1128; 2007.
Bernstein et al. The incidence of fracture among patients with inflammatory bowel disease. A population-based cohort study. Ann Intern Med 133(10): 795-799; 2000.
Van Staa, et al. Inflammatory bowel disease and the risk of fracture. Gastroenterology 125(6): 1591-1597; 2003.
Bryant et al. Systematic review: body composition in adults with inflammatory bowel disease. Aliment Pharmacol Ther 38(3): 213-225; 2013.
Wiskin et al. Body composition in childhood inflammatory bowel disease. Clin Nutr 30(1): 112-115; 2011.
Fields DA and Allison DB, Air-displacement plethysmography pediatric option in 2-6 years old using the four-compartment model as a criterion method. Obesity (Silver Spring). Aug. 2012;20(8):1732-7.
Mukhopadhya et al. IBD—what role do Proteobacteria play? Nature Reviews Gastroenterology & Hepatology vol. 9, pp. 219-230 (2012).

(Continued)

*Primary Examiner* — Christopher Adam Hixson
(74) *Attorney, Agent, or Firm* — K&L Gates LLP

(57) ABSTRACT

The present invention relates to a method for determining a level of fat-free body mass (FFM) in a paediatric subject comprising determining a level of phenylacetylglutamine (PAG) in a sample obtained from the subject.

20 Claims, No Drawings

(56) References Cited

OTHER PUBLICATIONS

De Bruin et al: "Measurement of fat-free mass in infants", Pediatric Research, vol. 38, No. 3, Sep. 1, 1995 (Sep. 1, 1995), pp. 411-417.
Dung et al: "Impedance index or standard anthropometric measurements, which is the better variable for predicting fat-free mass in sick children?", Acta Paediatrica, vol. 96, No. 6, Jun. 2007 (Jun. 2007), pp. 869-873.
Wells JCK and Fewtrell MS: "Measuring body composition", Archives of Disease in Childhood, vol. 91, No. 7, Jun. 14, 2005 (Jun. 14, 2005), pp. 612-617.
Wijeyesekera et al: "Quantitative UPLC-MS/MS analysis of the gut microbial co-metabolites phenylacetylglutamine, 4-cresyl sulphate and hippurate in human urine: INTERMAP Study", Analytical Methods, vol. 4, No. 1, Jan. 1, 2012 (Jan. 1, 2012), pp. 65-72.
Zheng et al: "NMR-Based Metabolomic Profiling of Overweight Adolescents: An Elucidation of the Effects of Inter-/Intraindividual Differences, Gender, and Pubertal Development", Biomed Research International, vol. 3, No. 1, Jan. 1, 2014 (Jan. 1, 2014), pp. 33-10.
Stiegler P and Cunliffe A: "The Role of Diet and Exercise for the Maintenance of Fat-Free Mass and Resting Metabolic Rate During Weight Loss Contents", Sports Med, Jan. 1, 2006 (Jan. 1, 2006).
Do Prado et al: "Effects of long-term multidisciplinary inpatient therapy on body composition of severely obese adolescents", Jornal De Pediatria, vol. 85, No. 3, Jun. 1, 2009 (Jun. 1, 2009), pp. 243-248.
International Search Report for PCT/EP2016/081841.
International Written Opinion for PCT/EP2016/081841.
Elliott et al., "Urinary Metabolic Signatures of Human Adiposity", Science Translational Medicine, vol. 7, Issue No. 285, Apr. 29, 2015, pp. 1-16.
Japan Patent Office Communication for Application No. P2018-529111, Dispatch No. 443593, Dispatch Date Nov. 4, 2020, 6 pages.

\* cited by examiner

METHOD FOR DETERMINING FAT FREE BODY MASS

CROSS-REFERENCES TO RELATED APPLICATIONS

The present application is the National Stage of International Application No. PCT/EP2016/081841, filed on Dec. 20, 2016, which claims benefit to European Application No. 15203045.8, filed Dec. 30, 2015. The entire contents of the above applications are incorporated by reference as if recited in full herein.

FIELD OF THE INVENTION

The present invention relates to a method for determining the level of fat-free body mass (FFM) in a paediatric subject. In particular, the present invention provides a non-invasive method for determining the level of FFM in a paediatric subject which utilizes molecular biomarkers.

BACKGROUND TO THE INVENTION

Around 25 percent of inflammatory bowel disease (IBD) patients are diagnosed during childhood (around their pubertal growth spurt) (Ezri et al; 2012; Digestion 85(4): 308-319).

Growth is a crucial process for pediatric subjects and growth failure/growth delay is a common feature of paediatric IBD. The etiology of this growth failure is complex and encompasses a reduction of caloric intake, malabsorption, micronutrients deficiency, delayed puberty, decreased physical activity and increased production of inflammatory cytokines (Sauer and Kugathasan; 2009; Gastroenterol Clin North Am 38(4): 611-628 & Ezri et al.; as above). In this context, accurate assessment of body composition in children with IBD is of critical importance, particularly given the relevance of pharmacotherapy and nutritional support for inducing disease remission, restoring growth and nutritional status.

Only a few studies have reported body composition in children with IBD (e.g. Boot et al.; Gut 42(2): 188-194; 1998; Azcue et al.; Gut 41(2): 203-208; 1997; Burnham et al.; Am J Clin Nutr 82(2): 413-420; 2005; Thayu et al.; Inflamm Bowel Dis 13(9): 1121-1128; 2007). Most of these studies showed that fat free mass (FFM) adjusted for age, height and maturation is generally reduced in children with IBD as compared to healthy children, whereas body fat mass is more stable. This cachexia status is also inversely correlated with the disease activity score (i.e. Pediatric CD Activity Index, PCDAI) and may have severe long term health consequences on bone health, muscle performance and quality of life (Bernstein et al.; Ann Intern Med 133(10): 795-799; 2000, van Staa, et al; Gastroenterology 125(6): 1591-1597; 2003; Bryant et al.; Aliment Pharmacol Ther 38(3): 213-225; 2013).

Body weight or body mass index (BMI) as a single parameter does not reflect changes in body composition induced by diseases or nutritional unbalance (Wiskin et al.; Clin Nutr 30(1): 112-115; 2011). Accordingly, body composition assessment provides valuable insights for care providers and nutritionists, particularly in the pediatric population.

There are a number of highly sophisticated techniques that can be used in research settings or in the clinic to assess body composition. All these techniques are subject to measurement error (between 1-6%) and have basic assumptions that can slightly differ.

Most of the assessment of body composition in the pediatric population is based on two compartments (i.e. body fat and FFM) that overestimate percentage (%) of body fat due to the biochemical immaturity of children (as compared to adults) driven by a higher amount of water and a lower proportion of minerals and proteins. In order to take into account the inter-individual variability in hydration and mineral content, multi-compartment models produce more accurate estimates of body composition. The 4-compartment model approach considered as a gold-standard method in adults and in pediatric populations divides the body into 4 elements such as water, proteins, minerals and fat. The sum of water, protein, mineral and glycogen is named fat free mass (FFM). It implies that body's fat mass is not directly measured but obtained by subtraction FFM from the body weight (Fields and Allison; Obesity (Silver Spring) 20(8): 1732-1737; 2012). This model needs various inputs such as body density, bone mineral content and total body water that are determined by several techniques such as dual-energy X-ray absorptiometry (DXA), isotopic dilution and hydrodensitometry. Such multi-compartment models have drawbacks of being costly (technically demanding) and time consuming and are mainly used for research purpose.

In the pediatric population, techniques such as DXA, air-displacement plethysmography, isotopic dilution and bioelectrical impedance analysis (BIA), and skinfold-thickness with anthropometric equations may be employed. Although expensive, DXA is an attractive technique but it is still difficult to establish as a gold-standard since the variability of the estimates may vary between suppliers, software and data collection. Skinfolds-thickness values using anthropometric equations remain the most general practice for paediatric care providers since it is a straightforward and easy methodology to implement. However, the most sensitive and specific method for use in pediatric population in general, and IBD in particular, is still a matter of debate.

In this context, doctors are faced to multiple methods at various costs and performance to measure body composition.

There is a need for additional methods for determining FFM in paediatric subjects.

SUMMARY OF THE INVENTION

The present inventors have determined that levels of particular metabolites correlate with the level of FFM in paediatric subjects. A nuclear magnetic resonance (NMR) spectroscopy approach has been used to assess metabolite profiles, and assess the composite metabolic signatures related to specific body composition, in particular FFM.

Accordingly, in a first aspect the present invention provides a method for determining a level of fat-free body mass (FFM) in a paediatric subject comprising determining a level of phenylacetylglutamine (PAG) in a sample obtained from the subject.

The subject may suffer from a condition which causes reduced FFM in said subject. For example, the condition may be inflammatory bowel disease (IBD), constitutional growth delay, general malnourishment, coeliac disease, cholestatic liver disease or hormonal deficiency.

In a preferred embodiment the condition is IBD.

The method may comprise the steps of:
(a) determining the level of PAG in a sample obtained from the subject;

(b) comparing the level of PAG in the sample to a reference value;
wherein the level of PAG in the sample compared to the reference value is indicative of the level of FFM in the subject.

The method may further comprise: (a) determining the level of one or more biomarkers selected from taurine, the PAG:cis-aconitate ratio and the PAG:urea ratio; and (b) comparing the levels of the one or more biomarkers in the sample to the one or more reference values; wherein the level of the one or more biomarkers in the sample compared to the reference value is indicative of the level of FFM in the subject.

The method may comprise determining the level of at least two biomarkers selected from taurine, the PAG:cis-aconitate ratio and the PAG:urea ratio in the sample from said subject. The method may comprise determining the level of each of taurine, PAG:cis-aconitate ratio and PAG:urea ratio in the sample from said subject.

In one embodiment, a level of PAG is determined and an increase in the level of PAG in the sample from the subject compared to the reference sample is indicative of higher levels of FFM.

In one embodiment, a level of taurine is determined and an increase in the level of taurine in the sample form the subject compared to the reference sample is indicative of higher levels of FFM.

In one embodiment, a PAG:cis-aconitate ratio is determined and an increase in the PAG:cis-aconitate ratio in the sample from the subject compared to the reference sample is indicative of higher levels of FFM.

In one embodiment, a PAG:urea ratio is determined and an increase in the PAG:urea ratio in the sample from the subject compared to the reference sample is indicative of the higher levels of FFM.

In one embodiment the reference value is based on a mean level of the biomarker in a control population of subjects.

The level of a biomarker may be determined by NMR spectrometry or mass spectrometry.

The sample may be a urine or blood sample.

In a further aspect, the present invention relates to a method for modulating the level of FFM in a paediatric subject identified as requiring treatment to increase FFM levels by the present method; comprising modifying a lifestyle of the subject to modulate the level of FFM. The method may involve repeating the aforementioned method after modifying the lifestyle of the subject.

In one embodiment modifying a lifestyle of the subject comprises a change in diet. The change in diet may comprise administering at least one nutritional product to the subject as part of a diet which promotes an increase in FFM.

In a further aspect the present invention provides a nutritional composition for use to increase FFM in a paediatric subject, wherein the subject is identified as requiring treatment to increase FFM by a method of the present invention.

In a further aspect the present invention relates to the use of a nutritional composition to increase FFM in a paediatric subject, wherein the subject is identified as requiring treatment to increase FFM by a method of the present invention.

DETAILED DESCRIPTION OF THE INVENTION

Fat-Free Mass (FFM)

In one aspect, the present invention relates to a method for determining the level of FFM in a paediatric subject.

FFM is generally used to refer broadly to the sum of water, protein, mineral and glycogen in the body. In other words, FFM is made up of the constituents of the body other than fat. FFM may also be referred to as lean mass.

Reduced levels of FFM are associated with a number of paediatric conditions which result in growth delay. Such growth delay may have severe long term health consequences on bone health, muscle performance and quality of life.

The present method may be used to identify a paediatric subject with low levels of FFM and to monitor the levels FFM in said subject during a lifestyle intervention (e.g. administration of a nutritional product to increase levels of FFM). In particular, the present invention involves determining the level of specific metabolites in a sample from the subject to assess levels of FFM. Accordingly, the present methods provide the advantage of being non-invasive methods which provide fast and reliable biomarkers which may be used for effective and individual FFM management in, for example, clinical or research settings in order to optimize nutritional and/or therapeutic solutions and restore quality of life.

Sample

The present method involves determining the level of a biomarker in a sample obtained from a subject. This sample may be referred to as the 'test sample'. Thus the present method is typically practiced outside of the human or animal body, e.g. on a body fluid sample that was previously obtained from the subject to be tested.

The sample may, for example, be a urine, serum or plasma sample.

The sample may be derived from blood, i.e. the sample comprises whole blood or a blood fraction. The sample may comprise blood plasma or serum.

Techniques for collecting blood samples and separating blood fractions are well known in the art. For instance, venous blood samples can be collected from patients using a needle and deposited into plastic tubes. The collection tubes may, for example, contain spray-coated silica and a polymer gel for serum separation. Serum can be separated by centrifugation at 1300 RCF for 10 min at room temperature and stored in small plastic tubes at −80° C.

In a preferred embodiment the sample is a urine sample.

Detection Method

The levels of PAG, and any other biomarker mentioned herein, in the sample may be measured or determined using any suitable method. For example, nuclear magnetic resonance (NMR) spectrometry may be used. Other methods, such as mass spectroscopic methods, chromatographic methods, labeling techniques, or quantitative chemical methods may be used in alternative embodiments. Typically the biomarker level in the sample and the reference value are determined using the same analytical method.

Subject

According to the present invention the subject is a paediatric subject.

Preferably the subject is a mammal, preferably a human. The subject may alternatively be a non-human mammal, including for example, a horse, cow, sheep or pig. In one embodiment, the subject is a companion animal such as a dog or a cat.

In one embodiment the subject is a human and the term paediatric refers to a subject less than 18 years of age. The subject may, for example, be between 10 and 18 years of age, between 8 and 12 years, between 8 and 14 years or between 10 and 12 years of age.

Biomarker

The present invention involves determining the levels of a biomarker, in particular the level of PAG, in a sample from a subject. Additional biomarkers may be selected from taurine, the ratio of PAG:cis-aconitate and the ratio of PAG:urea.

Accordingly, the present method involves measuring levels of at least one biomarker. By combining measurements of biomarkers an improved biomarker signature of FFM may be achieved.

Phenylacetylglutamine (PAG)

The present invention involves determining the level of PAG in a sample from a subject.

PAG (5-amino-5-oxo-2-[(1-oxo-2-phenylethyl)amino] pentanoic acid) is a product formed by the conjugation of phenylacetate and glutamine. Phenylacetate is generated from either host or gut-microbial metabolism. Glutamine is mainly generated from alpha-ketogluterate in the Krebs cycle.

PAG is a major nitrogenous metabolite that can be found, for example, in urine. Its levels closely reflect intermediates in the urea cycle and may be reflective of an alteration in nitrogen metabolism.

In one embodiment an increase in the level of PAG in the sample from the subject compared to the reference sample is indicative of higher levels of FFM.

Taurine

In one embodiment, the present method may involve determining the level of taurine.

Taurine (2-aminoethanesulfonic acid) is an organic acid widely distributed in tissues. It is a major constituent of bile and can be found in the large intestine. Taurine has many fundamental biological roles, such as conjugation of bile acids, antioxidation, osmoregulation, membrane stabilization, and modulation of calcium signaling. It is essential for cardiovascular function, and development and function of skeletal muscle, the retina, and the central nervous system. Taurine is unusual among biological molecules in being a sulfonic acid, while the vast majority of biologically occurring acids contain the more weakly acidic carboxyl group.

Taurine is a cysteine derivative. Mammalian taurine synthesis occurs in the pancreas via the cysteine sulfinic acid pathway. In this pathway, the thiol group of cysteine is first oxidized to cysteine sulfinic acid by the enzyme cysteine dioxygenase. Cysteine sulfinic acid, in turn, is decarboxylated by sulfinoalanine decarboxylase to form hypotaurine. It is unclear whether hypotaurine is then spontaneously or enzymatically oxidized to yield taurine.

In one aspect the present invention provides a method for determining a level of fat-free body mass (FFM) in a paediatric subject comprising determining a level of taurine in a sample obtained from the subject.

The method may comprise the steps of: (a) determining a level of taurine in a sample obtained from the subject; (b) comparing the levels of taurine in the sample to a reference value; wherein the level of taurine in the sample compared to the reference value is indicative of the level of FFM in the subject.

In one embodiment an increase in the level of taurine in the sample form the subject compared to the reference sample is indicative of higher levels of FFM.

In one embodiment, taurine may be substituted for PAG in a method of the present invention.

PAG:Cis-Aconitate Ratio

In one embodiment the present method may involve determining the level of cis-aconitate.

Cis-aconitate is the conjugate base of cis-aconitic acid (prop-1-ene-1,2,3-tricarboxylic acid). It is an intermediate in the isomerization of citrate to isocitrate in the citric acid cycle and is acted upon by the enzyme aconitase.

The present invention may involve determining the ratio of PAG to cis-aconitate (PAG:cis-aconitate ratio) in a sample from a paediatric subject.

In one embodiment a decrease in the level of cis-aconitate in the sample compared to the reference sample is indicative of higher levels of FFM. In one embodiment an increase in the PAG:cis-aconitate ratio in the sample from the subject compared to the reference sample is indicative of higher levels of FFM.

PAG:Urea Ratio

In one embodiment, the present method may involve determining the level of urea.

Urea (carbamide) is an organic compound with the chemical formula $CO(NH_2)_2$. The molecule has two $NH_2$ groups joined by a carbonyl ($C=O$) functional group.

Urea serves an important role in the metabolism of nitrogen-containing compounds by animals, and is the main nitrogen-containing substance in the urine of mammals. It is involved in many biochemical processes, most notably nitrogen excretion.

The present invention may involve determining the ratio of PAG to urea in a sample from a paediatric subject.

In one embodiment a decrease in the level of urea in the sample compared to the reference sample is indicative of higher levels of FFM. In one embodiment an increase in the PAG:urea ratio in the sample from the subject compared to the reference sample is indicative of higher levels of FFM.

Combinations of Biomarkers

Whilst determining the level of PAG has predictive value in the methods of the present invention, the quality and/or the predictive power of the methods may be improved by combining values from multiple biomarkers.

Thus the method of the present invention may involve determining the level of at least two biomarkers from those defined herein. For instance, the method may comprise determining the level of PAG and taurine; the level of PAG and the PAG:cis-aconitate ratio or the level of PAG and the PAG:urea ratio.

The method may comprise determining the level of PAG, the level of taurine and the PAG:cis-aconitate ratio.

The method may comprise determining the level of PAG, the level of taurine and the PAG:urea ratio.

The method may comprise determining the level of PAG, the PAG:cis-aconitate ratio and the PAG:urea ratio.

The method may comprise determining the level of PAG, the level of taurine, the PAG:cis-aconitate ratio and the PAG:urea ratio.

In a particularly preferred embodiment, the method comprises determining the level of PAG, the level of taurine, the PAG:cis-aconitate ratio and the PAG:urea ratio, where increased levels of PAG and taurine and an increased PAG:cis-aconitate ratio and an increased PAG:urea ratio is indicative of a greater level of FFM.

Comparison to Reference Levels

The present method may comprise a step of comparing the level of PAG and/or taurine and/or the PAG:cis-aconitate ratio and/or the PAG:urea ratio in the test sample with one or more reference or control values. The term reference level is synonymous with 'control level' and broadly includes data that the skilled person would use to facilitate the accurate interpretation of technical data.

Typically a specific reference value for each individual biomarker determined in the method is used. The reference value may be a normal level of that biomarker, e.g. a level of the biomarker in the same sample type (e.g. urine, serum or plasma) in a normal subject. The reference value may, for example, be based on a mean or median level of the biomarker in a control population of subjects, e.g. 5, 10, 100, 1000 or more normal subjects (who may either be age- and/or gender-matched or unmatched to the test subject—it is known in the art how to assign correct reference values as they will vary with gender, race, genetic heritage, health status or age, for example).

In some embodiments, the reference value is a value obtained previously from the same subject. This allows a direct comparison of the effects of an intervention (e.g. a change in diet) compared to a previous level prior to an intervention or a different intervention on biomarker levels associated with FFM, so that improvements can be directly assessed.

The reference value may be determined using corresponding methods to the determination of biomarker levels in the test sample, e.g. using one or more samples taken from normal subjects. For instance, in some embodiments biomarker levels in control samples may be determined in parallel assays to the test samples. Alternatively, in some embodiments reference values for the levels of individual biomarkers in a particular sample type (e.g. urine, serum or plasma) may already be available, for instance from published studies. Thus in some embodiments, the reference value may have been previously determined, or may be calculated or extrapolated, without having to perform a corresponding determination on a control sample with respect to each test sample obtained.

The control or reference levels for a biomarker as described herein in a particular sample may be stored in a database and used in order to interpret the results of the method as performed on the subject.

The level of a biomarker in a test sample, for example the level of the PAG in a sample from the subject, may be compared to the respective level of the same target in one or more cohorts (populations/groups) of control subjects. The control subjects may be selected from a cohort which have been diagnosed with reduced FFM and a cohort wherein the subjects have been predetermined not to have reduced FFM.

The reference value for the level of the biomarker as described herein is preferably measured using the same units used to characterize the level of biomarker in the test sample. Thus, if the level of the level the biomarker as described herein is an absolute value such as the units in μmol/l (μM) the reference value is also based upon the units in μmol/l (μM) in individuals in the general population or a selected control population of subjects.

In one embodiment the sample is urine and the level of a biomarker, as described herein, is typically expressed as μmol/mmol creatinine.

The present method provides that a difference in the level of a biomarker as described herein in the test sample compared to the reference level is indicative of the level of FFM.

The extent of the difference between the subject's biomarker levels and the corresponding reference values is also useful for determining which subjects would benefit most from certain interventions. The level of the biomarker in the test sample may be increased or decreased by, for example, at least 1%, at least 5%, at least 10%, at least 20%, at least 30% or at least 50% or at least 100% compared to the reference value.

In one embodiment, a higher level of a biomarker as described herein in the test sample compared to the reference level may be indicative of a higher level of FFM. The level of a biomarker as described herein may be for example, at least 1%, at least 5%, at least 10%, at least 20%, at least 30%, at least 50% or at least 100% greater in the test sample compared to the reference level.

In one embodiment, a lower level a biomarker as described herein in the test sample compared to the reference level may be indicative of a lower level of FFM. The level a biomarker as described herein may be for example, at least 1%, at least 5%, at least 10%, at least 20%, at least 30%, at least 50% or at least 100% greater in the test sample compared to the reference level.

Association of Biomarker Levels to FFM

In general, an increased level of the biomarkers described herein in the test sample compared to the reference value may be indicative of higher levels of FFM.

The overall level of FFM may be assessed by determining the levels of different biomarkers as discussed above. For instance, subjects may be stratified into low, medium, high and/or very high prediction of FFM level according to the number of individual biomarkers which are modulated relative to control and/or the degree to which they are elevated.

Condition

In one embodiment the paediatric subject suffers from a condition which causes reduced FFM in said subject.

Conditions associated with reduced FFM include, for example, inflammatory bowel disease (IBD), constitutional growth delay, general malnourishment, coeliac disease, cholestatic liver disease or hormonal deficiency.

In one embodiment the subject suffers from IBD. IBD refers to a group of inflammatory conditions of the colon and small intestine. The principle types of IBD are Crohn's disease and ulcerative colitis. Crohn's disease affects the small intestine and large intestine, and can also affect the mouth, esophagus, stomach and the anus; whereas ulcerative colitis primarily affects the colon and the rectum. Other types of IBD include collagenous colitis, lymphocytic colitis, diversion colitis, Behçet's disease, and indeterminate colitis.

IBD conditions may present with any of the following symptoms: abdominal pain, vomiting, diarrhea, rectal bleeding, severe internal cramps/muscle spasms in the region of the pelvis and weight loss. The most prevalent extraintestinal complication of IBD is anemia.

IBD arises as a result of the interaction of environmental and genetic factors. Alterations to enteral bacteria may contribute and IBD affected individuals have been found to have 30-50% reduced biodiversity of commensalism bacteria such as a decrease in Firmicutes (namely Lachnospiraceae) and Bacteroidetes (Mukhopadhya et al.; Nature Reviews Gastroenterology & Hepatology 9 (4): 219-230).

In one embodiment a paediatric subject suffering from a condition which causes reduced FFM in said subject may be in need of treatment to increase FFM levels.

A condition which causes a reduced FFM in a subject may be a condition associated with growth delay in the subject. As used herein, growth delay may also be referred to as growth failure or growth retardation.

Growth delay refers to the state where the growth of a child is below that generally expected for a child of that age. The causes of growth delay are typically complex, but may involve a reduction of caloric intake, malabsorption, micronutrient deficiency, delayed puberty, hormonal imbalance, decreased physical activity and increased production of inflammatory cytokines. Growth delay may be related to a reduction in the level FFM in a subject.

A subject suffering from a condition requiring treatment to increase FFM levels may be determined as being in need of treatment to promote catch-up growth. Catch-up growth generally refers to a period of growth in a subject who has previously suffered from growth delay. Following a subsequent period of catch-up growth, the subject has a level of growth which is more similar to that of a control, age-matched reference subject than the subject had prior to the period of catch-up growth. The catch-up growth may result in the subject having the growth expected for a subject of the same age. The catch-up growth may result in the subject having level of growth which is closer to that expected for a subject the same than the subject had prior to the period of catch-up growth, but not reaching the growth expected for a subject of the same age.

In one embodiment the subject in need of treatment to increase FFM is suffering from growth delay or a condition associated with growth delay.

In one embodiment the subject need of treatment to increase FFM is in need of treatment to promote catch-up growth.

Methods for Promoting Healthy Levels of FFM

In one aspect, the present invention provides a method for modulating the levels of FFM in a paediatric subject identified as requiring such modulation by the present method. Preferably, the method comprises modifying a lifestyle of the subject to modulate the level of FFM.

In another aspect, the present invention provides a method for modulating the levels of FFM in a paediatric subject which comprises (a) determining a level of FFM in the subject by a method of the present invention and (b) selecting an appropriate intervention strategy (e.g. a change in lifestyle and/or diet) for the subject, based on assessed risk level.

Typically if the subject is predicted to have acceptable levels of FFM, no intervention may be necessary. For instance, if the subject's predicted level of FFM is similar to the reference value, no pharmaceutical or nutritional therapy may be required. The reference value may correspond, for example, to a normal or mean level of FFM a control paediatric population.

Alternatively, if the subject is predicted to have reduced levels of FFM, the method may comprise modifying a lifestyle of the subject. The modification in lifestyle in the subject may be any change as described herein, e.g. a change in diet.

In one embodiment, a modification in lifestyle in the subject comprises a change in diet. Preferably, the change in diet comprises administering at least one nutritional product to the subject that is part of a diet that modulates levels of FFM e.g., promotes an increase in FFM.

As used herein, the term "promotes an increase in FFM" also encompasses preventing a decrease in FFM.

The nutritional product may be, for example, selected from food products, drinks, pet food products, food, nutraceuticals, food additives or nutritional formulas.

The nutritional product is usually to be taken orally, intragastrically or intravenously. Preferably, the nutritional product for use in the present invention is to be taken orally.

In one embodiment, the nutritional product may be for example, Modulen IBD, Peptamen or Nestrovit.

Preferably the change in diet is the use of at least one nutritional product that was previously not consumed or consumed in different amounts, e.g. a nutritional product that has an effect on levels of FFM. In particularly preferred embodiments, the change in diet comprises administering a nutritional composition which promotes an increase in FFM.

The lifestyle modification (e.g. change in diet) may be personalized to the subject, such that FFM levels are monitored in conjunction with a specific program targeted to modulate FFM levels in the subject. For instance, the method may comprise a further step of (re-)determining FFM levels in the subject (i.e. after the diet-based intervention), in order to assess the effectiveness of the therapy. For example, if the subject shows an increase in FFM levels after the initial intervention phase, the intervention may be continued to maintain the increase.

However, if the subject fails to respond adequately to the initial intervention (e.g. shows no significant change in FFM levels), the subject may be switched to an alternative program, e.g. a different diet or nutritional agent. For example, if a subject responds poorly to an initial nutritional regime, an alternative nutritional product may be administered to the subject. This process may be repeated, including selecting different dosages of individual agents, until a desired change in FFM levels is achieved. Typically, the subject may be maintained on a particular regime (e.g. a nutritional agent such as those defined above) for at least 1 week, 2 weeks, 1 month or 3 months before the determination of FFM levels is repeated.

In a further aspect, the present invention provides a nutritional agent as defined above (e.g. selected from food products, drinks, pet food products, food, nutraceuticals, food additives or nutritional formulas), for use in modulating levels of FFM in a subject, wherein a level of FFM in the subject has been predicted by a method as described above.

In a further aspect, the present invention provides use of a nutritional agent as defined above, for the manufacture of a medicament for modulating levels of FFM in a subject, wherein a level of FFM in the subject has been predicted by a method as described above.

Kits

In a further aspect, the present invention provides a kit for predicting the level of FFM in a paediatric subject. The kit may, for example, comprise one or more reagents, standards and/or control samples for use in the methods described herein. For instance, in one embodiment the kit comprises one or more reference samples comprising predetermined levels of (i) PAG; (ii) one or more of taurine, cis-aconitate and urea; and instructions for use of the kit for predicting FFM in a paediatric subject by comparing the predetermined levels in the reference sample to levels of biomarkers in a sample obtained from the subject.

Those skilled in the art will understand that they can freely combine all features of the present invention described herein, without departing from the scope of the invention as disclosed. The invention will now be described by way of example only with respect to the following specific embodiments.

EXAMPLES

Example 1—Determination of Urinary Biomarkers Correlated with FFM

Anthropometric assessment and urinary metabolite analysis was performed on a cohort of paediatric subjects with IBD and a control cohort.

Pearson correlation analysis indicated the levels PAG and taurine were positively correlated with FFM (see Table 1). In addition, the ratio of PAG:cis-Aconitate and the ratio of PAG:urea were also positively correlated with FFM (see Table 1).

TABLE 1

|  | Pearson Correlation Value | p-value |
|---|---|---|
| FFM-PAG | 0.36 | 0.02 |
| FFM-Taurine | 0.46 | 0 |
| FFM-PAG:cis-Aconitate | 0.38 | 0.01 |
| FFM-PAG:urea | 0.3 | 0.06 |

Materials & Methods

Experimental Design

This study was approved by the Ethical Committee of the University of Lausanne, Switzerland (protocol 69/10), and conducted in the Pediatric Gastroenterology outpatient clinic of the University Hospital of Lausanne, Switzerland. Eligible patients were aged between 10 and 18 years old, with a diagnosis of CD or UC, confirmed according to international criteria (Levin et al.; Journal of pediatric gastroenterology and nutrition; 2014 June; 58(6):795-806). The control group consisted of healthy subjects between 10 and 18 years of age without any family history of inflammatory bowel or other chronic inflammatory diseases. An informed written consent was obtained from the parents and an assent from each child.

Anthropometric Assessment

Body weight was measured using a calibrated digital scale (Seca, Hamburg, Germany) to the nearest 0.1 kg. Height was measured using a wall-mounted stadiometer (Holtain, Crosswell, UK) to the nearest 0.1 cm. Body mass index (BMI, $kg/m^2$) was determined by dividing the weight in kilograms by the square of the height in meters. Height velocity was calculated as the amount of growth in centimetres divided by the time interval between measurements in years. All values were expressed in z-scores. Pubertal stage was assessed according to Tanner score.

Body Composition

Bioimpedance analysis (BIA) was performed using Body Impedance Analyser Akern (Florence, Italy). While the subject was lying comfortably without his limbs touching, the body electrodes were placed just below the phalangeal-metacarpal joint in the middle of the dorsal side of the dominant hand and just below the metatarsal arch on the superior side of the foot of the same side. Fat free mass (FFM) was then calculated using the software BodyGram Pro® supplied by the manufacturer (which uses weight, age, and an impedance index ($height^2$/resistance)).

Disease Activity Index and Quality of Life for Patients with IBD

Disease activity was assessed using the Pediatric Crohn's Disease Activity Index (PCDAI), a 100 point scale where a score >30 indicates severe disease, and the Pediatric Ulcerative Colitis Activity Index (PUCAI)(31), a 85 points scale where a score >35 indicates severe disease.

Metabonomics Analysis

Morning spot urine samples were collected at baseline for all subjects, and at the 6-month and 12-month visit for the IBD patients. Urine samples (1 mL) were collected by means of sterile plastic tubes, and were stored at −80° C., prior to analysis. 40 µL of urine were mixed with 20 µL deuterated phosphate buffer solution 0.6 M $KH_2PO_4$, containing 1 mM of sodium 3-(trimethylsilyl)-[2,2,3,3-$2H_4$]-1-propionate (TSP, chemical shift reference $\delta_H$=0.0 ppm). The homogenates were centrifuged at 17,000 g for 10 minutes and 60 µL of the supernatant were transferred into 1.7 mm NMR tubes. $^1H$ NMR metabolic profiles were acquired with a BrukerAvance II 600 MHz spectrometer equipped with a 1.7 mm probehead 300 K (BrukerBiospin, Rheinstetten, Germany), using a standard pulse sequence with water suppression, and processed using TOPSPIN (version 2.1, Bruker, Germany) software package.

Statistical Analysis

Chemometric analysis was performed using the software package SIMCA-P+ (version 12.0, Umetrics AB, Umeå, Sweden). Principal component analysis (PCA) and a modification of Partial Least Squares Regression (PLSR) that removes all information orthogonal to the response variable during the fitting process were employed. This variant, Orthogonal Projection to Latent Structures (O-PLS) provides sparser models (improving their interpretability) with the same degree of fit as PLSR. To highlight the weight of individual variables in the model, Variable Importance in Projection (VIP) was used, with a value above 1 used as a threshold by convention. Influential metabolites were relatively quantified by signal integration and analysed using t-tests. Metabolic pathway analysis was conducted by performing a metabolite set enrichment analysis, using the web-based MetaboAnalyst 3.0 tool, to the list of influential metabolites obtained through multivariate data analysis. Visualization of the trajectories in the principal components (PC) space was performed using Plotly (Plotfly Technologies Inc., Montréal, Québec).

All publications mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A method for modulating a level of fat-free body mass (FFM) in a paediatric subject, the method comprising:
    determining a level of phenylacetylglutamine (PAG) in a sample obtained from the paediatric subject;
    comparing the level of PAG in the sample to a reference value of PAG;
    determining the level of FFM in the paediatric subject, wherein the level of PAG in the sample compared to the reference value of PAG is indicative of the level of FFM in the subject;
    based on the level of FFM, identifying the paediatric subject as requiring treatment to increase the level of FFM; and
    modulating the level of FFM in the subject by modifying a lifestyle of the subject.

2. The method according to claim 1, further comprising:
    determining levels of one or more biomarkers selected from the group consisting of taurine, PAG:cis-aconitate ratio and PAG:urea ratio in the sample; and
    comparing the levels of the one or more biomarkers in the sample to one or more reference values of the one or more biomarkers;
    wherein the levels of the one or more biomarkers in the sample compared to the one or more reference values of the one or more biomarkers are indicative of the level of FFM in the subject.

3. The method according to claim 2, comprising determining the levels of at least two biomarkers selected from the group consisting of taurine, PAG:cis-aconitate ratio and PAG:urea ratio in the sample from said subject.

4. The method according to claim 3, comprising determining the level of each of taurine, PAG:cis-aconitate ratio and PAG:urea ratio in the sample from said subject.

5. The method according to claim 1, wherein the level of PAG is determined and an increase in the level of PAG in the sample from the subject compared to the reference value of PAG is indicative of a higher level of FFM in the subject.

6. The method according to claim 2, wherein the level of taurine is determined and an increase in the level of taurine in the sample from the subject compared to the reference value of taurine is indicative of a higher level of FFM in the subject.

7. The method according to claim 2, wherein the PAG:cis-aconitate ratio is determined and an increase in the PAG:cis-aconitate ratio in the sample from the subject compared to the reference value of PAG:cis-aconitate ratio is indicative of a higher level of FFM in the subject.

8. The method according to claim 2, wherein the PAG:urea ratio is determined and an increase in the PAG:urea ratio in the sample from the subject compared to the reference value of PAG:urea ratio is indicative of a higher level of FFM in the subject.

9. A method for modulating a level of fat-free body mass (FFM) in a paediatric subject, the method comprising:
determining the level of FFM in the paediatric subject by determining a level of phenylacetylglutamine (PAG) in a sample obtained from the paediatric subject, wherein the level of the PAG is determined by nuclear magnetic resonance (NMR) spectrometry or mass spectrometry;
based on the level of FFM, identifying the paediatric subject as requiring treatment to increase the level of FFM; and
modulating the level of FFM by modifying a lifestyle of the subject.

10. The method according to claim 1, wherein the sample is a urine or blood sample.

11. A method for modulating a level of fat-free body mass (FFM) in a paediatric subject, the method comprising:
determining the level of fat-free body mass (FFM) in the paediatric subject by determining a level of phenylacetylglutamine (PAG) in a sample obtained from the paediatric subject, wherein the sample is a urine or blood sample;
based on the level of FFM, identifying the paediatric subject as requiring treatment to increase the level of FFM; and
modulating the level of FFM by modifying a lifestyle of the subject.

12. The method according to claim 11, wherein the subject suffers from a condition which causes reduced FFM in said subject.

13. The method according to claim 12, wherein the condition is inflammatory bowel disease (IBD), constitutional growth delay, malnourishment, coeliac disease, cholestatic liver disease or hormonal deficiency.

14. The method according to claim 12, wherein the condition is IBD.

15. The method according to claim 11, wherein the modifying a lifestyle of the subject comprises a change in diet.

16. The method according to claim 15, wherein the change in diet comprises administering at least one nutritional product to the subject as part of the diet which promotes an increase in FFM.

17. The method according to claim 2, wherein the reference value of PAG and the reference values of the one or more biomarkers are based on a mean level of PAG and mean levels of the one or more biomarkers respectively in a control population of normal paediatric subjects.

18. The method according to claim 2, wherein the levels of the one or more biomarkers are determined by nuclear magnetic resonance (NMR) spectrometry or mass spectrometry.

19. The method according to claim 4, wherein a combination of increased levels of PAG and taurine, an increased PAG:cis-aconitate ratio and an increased PAG:urea ratio in the sample from the subject compared to the reference values of PAG, taurine, the PAG:cis-aconitate ratio and the PAG:urea ratio respectively is indicative of a higher level of FFM in the subject.

20. The method according to claim 1, wherein a decrease in the level of PAG in the sample compared to the reference value of PAG is indicative of a lower level of FFM in the subject, and the subject with the lower level of FFM is identified as requiring treatment to increase the level of FFM.

* * * * *

UNITED STATES PATENT AND TRADEMARK OFFICE
CERTIFICATE OF CORRECTION

PATENT NO. : 10,935,543 B2
APPLICATION NO. : 15/778738
DATED : March 2, 2021
INVENTOR(S) : Martin et al.

It is certified that error appears in the above-identified patent and that said Letters Patent is hereby corrected as shown below:

On the Title Page

Item [72], replace "Omella"; with --Ornella;--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*